United States Patent
Sherr et al.

(10) Patent No.: US 10,941,194 B2
(45) Date of Patent: Mar. 9, 2021

(54) METHODS OF DIAGNOSING AND TREATING AUTISM SPECTRUM DISORDERS

(71) Applicant: The Regents of the University of California, Oakland, CA (US)

(72) Inventors: Elliot H. Sherr, Oakland, CA (US); Alireza Faridar, Oakland, CA (US)

(73) Assignee: The Regents of the University of California, Oakland, CA (US)

(*) Notice: Subject to any disclaimer, the term of this patent is extended or adjusted under 35 U.S.C. 154(b) by 461 days.

(21) Appl. No.: 15/545,621

(22) PCT Filed: Jan. 22, 2016

(86) PCT No.: PCT/US2016/014623
§ 371 (c)(1),
(2) Date: Jul. 21, 2017

(87) PCT Pub. No.: WO2016/118924
PCT Pub. Date: Jul. 28, 2016

(65) Prior Publication Data
US 2018/0002410 A1 Jan. 4, 2018

Related U.S. Application Data

(60) Provisional application No. 62/106,560, filed on Jan. 22, 2015.

(51) Int. Cl.
*C07K 16/18* (2006.01)
*G01N 33/68* (2006.01)

(52) U.S. Cl.
CPC ......... *C07K 16/18* (2013.01); *G01N 33/6896* (2013.01); *G01N 2333/916* (2013.01); *G01N 2333/9121* (2013.01); *G01N 2440/14* (2013.01); *G01N 2800/50* (2013.01)

(58) Field of Classification Search
None
See application file for complete search history.

(56) References Cited

U.S. PATENT DOCUMENTS

2010/0092473 A1  4/2010  Muraca et al.

FOREIGN PATENT DOCUMENTS

| WO | 2004044218 A2 | 5/2004 |
|---|---|---|
| WO | 2010083044 A1 | 7/2010 |
| WO | 2010093450 A2 | 8/2010 |
| WO | 2011031786 A2 | 3/2011 |
| WO | WO 2014/172490 | * 10/2014 |

OTHER PUBLICATIONS https://dictionary.cambridge.org/us/dictionary/english/system; 7 pages total, downloaded Nov. 22, 2019 (Year: 2019).*
Samantha A. Byrnes and Bernhard H. Weigl, Expert Review of Molecular Diagnostics, 2018; 18: 19-26 (Year: 2018).*
Vithayathil et al., Prog Brain Res. 2018; 241: 63-112 (Year: 2018).*
Bhattacharya et al. (PLoS One 12(3): e0171355. https://doi.org/10.1371/journal.pone.0171355; 22 pages total (Year: 2017).*
Piche-Nicholas et al., MAbs. 2018; 10: 81-94. doi: 10.1080/19420862.2017.1389355 (Year: 2018).*
Winkler, Ther. Deliv. 2013; 4: 791-809 (Year: 2013).*
Jafarlou et al., Journal of Biological Regulators & Homeostatic Agents, 2016: 30: 315-321 (Year: 2016).*
PCT/US2016/014623, "International Search Report and Written Opinion", dated Apr. 1, 2016, 12 pages.

* cited by examiner

*Primary Examiner* — Christina M Borgeest
(74) *Attorney, Agent, or Firm* — Kilpatrick Townsend & Stockton LLP

(57) ABSTRACT

The invention describes a method of diagnosing an individual as having an increased likelihood of having an autism spectrum disorder and in some instances, selecting a therapy. The invention is related to a system or a kit for performing such a method.

3 Claims, 2 Drawing Sheets

METHODS OF DIAGNOSING AND TREATING AUTISM SPECTRUM DISORDERS

CROSS-REFERENCES TO RELATED APPLICATIONS

This application is a U.S. National Phase Application of PCT/US2016/014623, filed Jan. 22, 2016 which claims priority to U.S. Provisional Patent Application No. 62/106,560, filed Jan. 22, 2015, the disclosure of which is hereby incorporated by reference in its entirety for all purposes.

BACKGROUND OF THE INVENTION

Autism spectrum disorders (ASD) affect an estimated 1 in 68 children in the United States. They are characterized by impairments in social interaction, verbal communication, and repetitive behaviors. The clinical diagnosis, which includes individuals with any one of a spectrum of neurodevelopmental conditions (including classical autism, Rett syndrome, pervasive developmental disorder-not otherwise specified, and Asperger syndrome), is four times more prevalent in boys than girls.

Children with ASD demonstrate deficits in social interaction, verbal and nonverbal communication, and repetitive behaviors or interests. In addition, they will often have unusual responses to sensory experiences, such as certain sounds or the way objects look.

Each of these symptoms range in severity from mild to severe. The symptoms can present in each individual child differently. For instance, a child may have little trouble learning to read but exhibit extremely poor social interaction. Each child will display communication, social, and behavioral patterns that are individual but fit into the overall diagnosis of ASD.

Children with ASD do not follow the typical patterns of child development. In some children, hints of future problems may be apparent from birth. In most cases, the problems in communication and social skills become more noticeable as the child lags further behind other children the same age. Often times between 12 and 36 months old, the differences in skills and other unusual behaviors become apparent. Some parents report the change as being sudden, and that their children start to reject people, act strangely, and lose language and social skills they had previously acquired. In other cases, there is a plateau of progress so that the difference between the child with and other children the same age becomes more noticeable.

At present, clinicians rely on behavioral characteristics to make a diagnosis of ASD. Some of the characteristic behaviors of ASD and/or autism can be apparent in the first few months of a child's life, or they can appear at any time during the early years. For the diagnosis, problems in at least one of the areas of communication, socialization, or restricted behavior must be present before the age of 3. The diagnosis requires a two-stage process. The first stage involves developmental screening during "well child" check-ups; the second stage entails a comprehensive evaluation by a multidisciplinary team.

There is evidence showing a clinical improvement in children with ASD in response to behavioral intervention treatment. Treatments such as the Denver Early Start model can result in improved cognitive and adaptive behavior, and reduced severity of the disorder (Dawson et al., Pediatrics, 2010, 125(1): e17-23).

It has been shown that mutations in single genes or chromosomal copy number variants (CNV) can lead to ASD. However, the most common genetic modifications associated with ASD such as CNV on 15q and 16p11.2 each individually only account for 0.5-1% of the diagnosed cases. There is also evidence suggesting that inherited genetic factors, which are likely polygenic and in utero environmental exposure play a role in the etiology of the disorder. Thus, these findings suggest that relying solely on de novo genetics is insufficient for diagnosing ASD.

Recent progress in ASD genetics has begun to point toward shared molecular mechanisms. One important advance is that key intersecting intracellular signaling pathways play a role in ASD. ASD is a common co-morbidity in rare syndromes (e.g., Costello, Noonan, LEOPARD, and cardio-facio-cutaneous syndromes), that are caused by mutations in signaling molecules immediately upstream of ERK (MEK, RAF, and RAS) (Samuels et al., Neuron, 2009, 61(2):160-7). Similarly, ERK is hyperphosphorylated in Fragile X syndrome patients, and administration of a metabotropic glutamate receptor (mGluR) antagonist that improves behavior also decreases ERK phosphorylation in animal models of Fragile X (Michalon et al., Neuron, 2012, 74(1):49-56). In addition, genetic and functional studies suggest that over-activation of protein kinase B (AKT) and phosphatidylinositide 3-kinase (PI3K) lead to ASD syndromes associated with macrocephaly (Riviere et al., Nat Genet, 2012, 44(8):934-40). Conversely, it has also been reported that genetic haploinsufficiency of AKT3 leads to ASD with microcephaly (Boland et al., Am J Hum Genet, 2007, 81(2):292-303). Moreover, genetic mutations of signaling molecules upstream and downstream of AKT/PI3K: the tuberous sclerosis complex (TSC1 and TSC2), phosphatase and tensin homolog deleted on chromosome 10 (PTEN), and mammalian target of rapamycin (mTOR) also can cause ASD and macrocephaly (Hobert et al., Eur J Hum Genet, 2013, 22: 273-76; Zhou and Parada, Curr Opin Neurobiol, 2012, 22(5):873-9; Rodriguez-Escudero et al., Hum Mol Genet, 2011, 20(21):4132-42; Ehninger and Silva, Trends Mol Med, 2011, 17(2):78-87). Moreover, disorders such as Fragile X and the Mecp2 duplication also indirectly lead to increases in ERK signaling (Hu et al., J Neurosci, 2008, 28(31):7847-62; Kim et al., Proc Natl Acad Sci USA, 2008, 105(11):4429-34; Michalon et al., Neuron, 2012, 7491):49-56; Jiang et al., J Neurosci, 2013, 33(50):19518-33) as does in utero exposure to valproic acid, which is a well-known environmental cause of ASD (Christensen et al., JAMA, 2013, 24(29):1696-703; Hao et al., J Neurosci, 2004, 24(29):6590-9). Furthermore, treatment with an mGluR antagonist, like Fragile X above, improves social behavior, likely through downregulation of ERK signaling (Mehta et al, PLoS One, 2011, 6(10):e26077). Another unanticipated linkage of ERK signaling to ASD is seen in patients with deletion of the 593 kb region in 16p11.2 (Weiss et al., N Engl J Med, 2008, 358(7):667-75). This chromosomal locus contains ERK1, but we have shown that the degree of ERK1 and ERK2 phosphorylation is paradoxically increased in cells from patients who only have one copy of this genomic region.

In some instances, the AKT/PI3K pathway may also be disrupted. In tuberous sclerosis, the TSC1 and TSC2 heterodimeric complex regulates the signaling pathway from the kinase AKT to mTOR and downstream protein synthesis and this pathway has been implicated in autism [24]. Similarly, PTEN and PI3K are upstream of these signaling molecules and there is increasing evidence linking both to autism (Levitt and Campbell, J Clin Invest, 2009, 119(4):

747-54). Indeed, one of the more common physical findings in autism, relative macrocephaly, can result from abnormal PTEN signaling (Zhou and Parada, supra) while overt macrocephaly with autism is seen in Bannayan-Riley-Ruvalcaba and Cowden syndrome, which are allelic and caused by autosomal dominant mutations in PTEN (Boccone et al., Am J Med Genet A, 2006, 140(18):1965-9). Indeed, the reciprocal microcephaly and macrocephaly association with ASD extends beyond PTEN. The 16p11.2 deletion carriers have relative macrocephaly, while the duplication carriers have smaller heads (Zufferey et al., J Med Genet, 2012, 49(10): 660-8). Similarly, the "RAS-opathy" patients, who have activation of RAS and ERK signaling are often macrocephalic and show signs of brain overgrowth, which includes crowding of the posterior fossa and resultant Chiari I malformations (Croonen et al., Mol Syndromol, 2013, 4(5):227-34; Gripp et al., Am J Med Geneta, 2010, 152A(5):1161-8). Thus, it is possible that this change in head (and by inference, brain) size, may link ERK, PTEN and other signaling molecules together in a manner that suggests there are common pathways altered in many cases of ASD. In addition to the direct association of each of these pathways, there is also considerable cross-talk between the ERK pathway and the PI3K-AKT-TSC-mTOR pathway (Mendoza et al., Trends Biochem Sci, 2011, 36(6):320-8). For example ERK phosphorylates mTORC1 and AKT can downregulate RAF (Mendoza et al., supra).

Recently it has been shown that the activation state of various signaling pathways in the brain can be measured through sampling of peripheral blood. In fact, a correlation between the degree of activation of specific kinases in blood and brain in a mouse ASD model was found (Faridar et al., Molecular Autism, 2014, 5:57), as well as a similar correlation between brain and blood in two selected ASD syndromic disorders, Fragile X and the 600 kb chromosomal deletion syndrome at 16p11.2 (which contains MAPK3, the gene for ERK1).

BRIEF SUMMARY OF THE INVENTION

In one aspect, provided herein is a method of detecting whether an individual has an increased likelihood of having an autism spectrum disorder. The method includes obtaining a sample from a human individual; detecting a quantity of phosphorylated and total amounts of ERK, PTEN and AKT protein in the sample; determining the ratio of (i) phosphorylated ERK to total ERK and (ii) phosphorylated PTEN to total PTEN, and calculating the difference of the ratios from corresponding normal healthy control ratios, thereby generating a measure of difference of phosphorylated ERK and PTEN compared to control; comparing said measure to a ratio of phosphorylated AKT to total AKT of the individual, thereby generating a biomarker value; and analyzing the biomarker value relative to a control biomarker value, thereby detecting the predicted likelihood of presence or absence of an autism spectrum disorder in the individual.

The step of calculating the difference of the ratios can comprise $[(p\text{-}ERK/ERK)_{patient}-(p\text{-}ERK/ERK)_{control}]^2$ and $(p\text{-}PTEN/PTEN)_{patient}-(p\text{-}PTEN/PTEN)_{control}]^2$. The step of generating the measure of difference can comrpise $\{[(p\text{-}ERK/ERK)_{patient}-(p\text{-}ERK/ERK)_{control}]^2+[(p\text{-}PTEN/PTEN)_{patient}-(p\text{-}PTEN/PTEN)_{control}]^2\}$. The biomarker value can be equal to (corresponds to) $\{[(p\text{-}ERK/ERk)_{patient}-(p\text{-}ERK/ERK)_{control}]^2+[(p\text{-}PTEN/PTEN)_{patient}-(p\text{-}PTEN/PTEN)_{control}]^2\}/[(p\text{-}AKT/AKT)_{patient}]^2$.

In some embodiments, the determining and comparing steps of the method are performed using on a computer.

In some embodiments, the sample includes peripheral blood mononuclear cells (PBMCs). In some instances, the sample is whole blood containing PBMCs. In other instances, the sample is enriched for PBMCs. The sample may be isolated PBMCs.

The individual (test subject) can be determined to have an increased likelihood of an autism spectrum disorder based on the comparison of the individual's biomarker value and one or a set of control values. In some instances, the control value represents a biomarker value from a control individual who does not have an ASD or a control individual who is normal and healthy. In other instances, the control value represents a biomarker value from a group of control individuals who do not have an ASD or control individuals who are normal and healthy. The control individual may be age-matched and/or gender-matched to the test subject. If the biomarker value is higher or lower than the control value(s), the individual is likely to have an increased risk of having an ASD. In some instances, the individual has an ASD.

The method described above can also include testing the individual for behavior or other symptoms indicative of the presence of autism spectrum disorder. The method can further include administering an ameliorative treatment to the individual to reduce at least one, e.g., 1, 2, 3, 4, 5, or more, autism spectrum disorder symptoms. In some embodiments, the ameliorative treatment comprises a behavior intervention. The ameliorative treatment can include a method of reducing the level of the phosphorylated ERK signaling polypeptide or reducing ERK activity. The ameliorative treatment can include a method of modulating the level of the phosphorylated PTEN signaling polypeptide or reducing PTEN activity. The ameliorative treatment can include a method of modulating the level of the phosphorylated AKT signaling polypeptide or reducing AKT activity. In some embodiments, the method includes administering a treatment that modulates one or more polypeptides of the ERK pathway, PTEN pathway, AKT pathway, or any combination thereof. In some cases, the treatment includes a behavior intervention alone, or in combination with a pharmaceutical treatment.

In a second aspect, provided herein is a system for predicting whether an individual has ASD. The system includes a reagent that specifically detects phosphorylated ERK; a reagent that specifically detects total ERK; a reagent that specifically detects phosphorylated PTEN; a reagent that specifically detects total PTEN; a reagent that specifically detects phosphorylated AKT; a reagent that specifically detects total AKT; and a computer readable medium that includes instructions for (a) determining the ratio of (i) phosphorylated ERK to total ERK and (ii) phosphorylated PTEN to total PTEN and calculating the differences of those ratios from corresponding normal healthy ratios thereby generating a measure of difference of phosphorylated ERK and PTEN compared to controls (e.g., determining $\{[(p\text{-}ERK/ERK)_{patient}-(p\text{-}ERK/ERK)_{control}]^2+[(p\text{-}PTEN/PTEN)_{patient}-(p\text{-}PTEN/PTEN)_{control}]^2\}$); (b) comparing said measure to a ratio of phosphorylated AKT to total AKT of the individual, thereby generating a biomarker value (e.g., $\{[(p\text{-}ERK/ERK)_{patient}-(p\text{-}ERK/ERK)_{control}]^2+[(p\text{-}PTEN/PTEN)_{patient}-(p\text{-}PTEN/PTEN)_{control}]^2\}/[(p\text{-}AKT/AKT)_{patient}]^2$); and comparing the biomarker value to a control value.

In a third aspect, provided herein is also a kit for predicting whether an individual has ASD. The kit includes a reagent that specifically detects phosphorylated ERK; a reagent that specifically detects total ERK; a reagent that specifically detects phosphorylated PTEN; a reagent that specifically detects total PTEN; a reagent that specifically detects phosphorylated AKT; a reagent that specifically detects total AKT.

Other objects, features, and advantages of the present invention will be apparent to one of skill in the art from the following detailed description and figures.

DETAILED DESCRIPTION OF THE INVENTION

I. Introduction

Figure 1A:
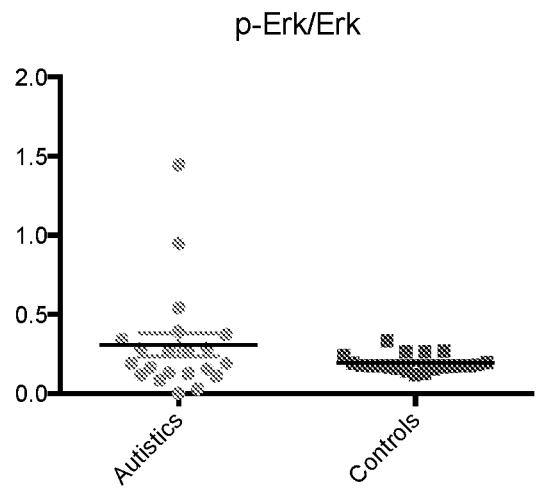
FIG. 1A-1C shows a plot of ratios of phosphorylated ERK/total ERK protein (FIG. 1A), phosphorylated PTEN/total PTEN protein (FIG. 1B), and phosphorylated AKT/total AKT protein (FIG. 1C), as measured by western blot analysis from peripheral blood mononuclear cell (PBMC) samples from patients having ASD and controls.

The present disclosure is based, in part, on the discovery of biomarkers and a diagnostic method for detecting autism spectrum disorder from an individual's sample. In some cases, the sample comprises peripheral blood mononuclear cells. The disclosure provides methods of detecting whether an individual has an increased likelihood of having an autism spectrum disorder using a mathematical model that combines the activity of the RAS/ERK and PTEN/AKT signaling pathways into a diagnostic value. Also provided herein are systems and kits for performing the method. Such methods allow for early detection of an autism spectrum disorder than currently available, thus enabling earlier ameliorative action to be taken than otherwise possible.

II. Definitions

As used herein, the following terms have the meanings ascribed to them unless specified otherwise.

A recitation of "a", "an" or "the" is intended to mean "one or more" unless specifically indicated to the contrary.

The terms "comprise," "comprising," "include," "including," "have," and "having" are used in the inclusive, open sense, meaning that additional elements may be included. The terms "such as," "e.g.," as used herein are non-limiting and are for illustrative purposes only. "Including" and "including but not limited to" are used interchangeably.

The term "autism spectrum disorder" or "ASD" refers to a group of developmental disabilities that can cause significant social, communication and behavioral challenges. ASDs affect each person in different ways, and the range of symptoms can exist from very mild to severe. Symptoms and their respective ranges include measured intelligence from intellectual disability to gifted, social interaction (e.g., making eye contact, enjoying interactions with others) from not interested in other to a variety of friendships, communication from non-verbal to verbal, repetitive behaviors from intense to mild, sensory response from not very sensitive to very sensitive, and motor skills from uncoordinated to coordinated. Additional descriptions of autism spectrum disorders and diagnostic classifications can be found in, for example, American Psychiatric Association. (2013). *Diagnostic and Statistical Manual of Mental Disorders: DSM*-5. Washington, D.C.: American Psychiatric Association; *Autism Spectrum Disorders: A Research Review for Practitioners*, Ozonoff, et al., eds., 2003, American Psychiatric Pub; Gupta, *Autistic Spectrum Disorders in Children,* 2004, Marcel Dekker Inc; and Hollander, *Autism Spectrum Disorders,* 2003, Marcel Dekker Inc.

The terms "individual," "subject," and "patient" are used interchangeably and refer to humans.

"Peripheral blood mononuclear cell" or "PBMC" is a mononuclear blood cell. Examples of a PBMC are, but not limited to, a lymphocyte (e.g., T cell, B cell, or natural killer cell), a monocyte, a dendritic cell, and a macrophage. PBMCs can be extracted or isolated from a whole blood sample. Methods for isolating PBMCs from whole blood can include density gradient centrifugation (e.g., using the Ficoll-hypaque method) and variations thereof.

The term "modulate" refers to a change in the biological activity of a biologically active molecule. Modulation can be an increase or a decrease in activity, a change in binding characteristics, or any other change in the; biological, functional, or immunological properties of biologically active molecules.

The terms "hyperphosphorylated," "phosphorylated," "phospho," and variants thereof refer to a post-translational modification of protein in which a covalently bound phosphate group is added to a serine, threonine or a tyrosine residue by a protein kinase.

The term "administering" or "administration" of a drug to a subject includes both direct administration, including self-administration, and indirect administration, including the act of prescribing a drug. For example, as used herein, a physician who instructs a patient to self-administer a drug and/or provides a patient with a prescription for a drug is administering the drug to the patient.

The term "reduction" of a symptom or symptoms refers to decreasing of the severity or frequency of the symptom(s), or elimination of the symptom(s).

The term "control value" refers to a biomarker value from an individual who does not have an autism spectrum disorder. The control value can represent a value from a normal, healthy individual. In some instances, the control value is from an individual who is age-matched and/or gender-matched to the test individual.

III. Detailed Description of the Embodiments

A. ERK and AKT/PTEN Signaling Pathway Polypeptides

The present disclosure relates to a biomarker-based diagnostic method for detecting the likelihood of having ASD, by detecting the level of phosphorylated and total ERK, PTEN and AKT protein in a sample obtained from an individual, and determining the likelihood of having ASD based on a biomarker value. Such a biomarker value can be determined from the ratios of phosphorylated ERK to total ERK, phosphorylated PTEN to total PTEN and phosphorylated AKT and total AKT. The inventors have discovered that the presence of aberrant activation of ERK and AKT/PTEN signaling pathways is indicative of having an increased likelihood of having an ASD.

The individual can be a human child such as a toddler at about 3 years old or younger, or a child older than 3 years old, e.g., a 4 year old, 5, year old, 6 year old, 7 year old, 8 year old, 9 year old or older. The individual can be an adolescent, e.g., about 10 year old to about 19 year old, or an adult, e.g., older than about 19 years old.

In some embodiments, the method comprises (a) measuring the level of one or a plurality of phosphorylated and total ERK signaling polypeptides and AKT/PTEN signaling polypeptides and (b) determining the ratios of the phosphorylated to total signaling polypeptides. The method also includes calculating the difference of the individual's ratios compared to those of a normal, healthy control. A control can be an individual that does not have ASD or can represent an average or range of normal values.

In some embodiments, the ERK signaling polypeptides includes signaling polypeptides of the ERK signaling pathway such as, but limited to, ERK1, ERK2, A-RAF, B-RAF, C-RAF, MEK1, MEK2, RSK1, RSK2, RSK3 and RSK4. The ERK signaling pathway is activated by a wide variety of receptors and ion channels involved in cell growth and differentiation. Downstream of the receptors (e.g., receptor tyrosine kinases) are a set of adaptor proteins linking the receptor to a guanine nucleotide exchange factor transducing the signaling to small GTP binding proteins, which in turn activate the core unit of the signaling pathway composed of a series of kinases such as A-RAF, B-RAF, C-RAF, MAPKKKs, MEK1/2 (MAPKK), ERK1/2 (MAPK), and CREB. When ERK1/2 dimer is phosphorylated, and thus activated, it can regulate target proteins (RSK1-4) in the cytosol and translocate to the nucleus where it phosphorylates various transcription factors regulating gene expression. In some embodiments, the method includes measuring the level of phosphorylated ERK and the level of total ERK in a subject's sample.

In some embodiments, the AKT/PTEN signaling polypeptides includes signaling polypeptides of the AKT/PTEN signaling pathway, such as GAB, PI3K, PTEN, AKT (e.g., AKT1, AKT2, AKT3), ARK, ATM, PDK1, mTOR (e.g., mTORC1, mTORC2), TSC1, TSC2, RHEB, S6K, 4E-BP, and GSK3. In some embodiments, the method includes measuring the level of phosphorylated PTEN and the level of total PTEN in a subject's sample. The method can also include measuring the level of phosphorylated AKT and the level of total AKT in the subject's sample.

In other embodiments, the method includes detecting the level of one or more phosphorylated and total RAS/MAPK signaling pathway polypeptides, such as, but not limited to, RAS, MEK1/2, cyclin D1, ERK1/2 (MAPKs), MEK1/2 (MAPKK), MNK1/2, B-RAF, C-RAF, MAP2K1, MAP2K2, RSK1, RSK2, RSK3, RSK4, TSC1, TSC2, Rheb, PRAK, MAPKAPK-2, MAPKAPK-3, p90RSK, KSR1, and MSK1/2. Optionally, the method can include detecting the level of one or more phosphorylated and total AKT/PI3K signaling pathway polypeptides, such as, but not limited to, PI3K (e.g., PIK3CA, PIK3R1), GSK3f3, TSC1, TSC2, PRAS40, PDK1, GAB1, GAB2, p53, p27 Kips, and p21 Waf1/Cip1. The method can also include detecting the level of activated or total SHANK3, GRM1, GRMS, ARC, EIF4E, HOMER1, FMR1, Wee1, or UBE3A

B. Methods of Measuring Signaling Pathway Polypeptides

The level of phosphorylated polypeptides and total polypeptides of the ERK and AKT/PTEN signaling pathways can be detected in sample taken from a human individual. In some embodiments, the sample comprises peripheral mononuclear blood cells (PBMCs). The sample can be whole blood. Alternatively, the sample can include isolated PBMCs. The sample may be enriched for PBMCs.

Proteins can be extracted from the sample by lysing the cells using standard reagents, such as a Trizol solution. The proteins can be precipitated and treated with a solution containing protease and/or phosphatase inhibitors. The protein extract can be solubilized with, for example, 10 M Urea/50 mM DTT. For some applications, the protein extract can be reduced and alkylated. In some instances, the extract is also digested with trypsin. Phosphorylated proteins can be purified from the trypsin digested extract by using a titanium dioxide column and eluting in potassium dihydrogen phosphate (e.g., 1 M potassium dihydrogen phosphate).

An antibody that specifically binds to a phosphorylated ERK and AKT/PTEN signaling pathways polypeptide can be used to measure its level in a sample. For example, commercial antibodies specific to the phosphorylated domains of the ERK or AKT/PTEN signaling pathways polypeptide can be used. Commercial antibodies are available from ABCAM®, CELL SIGNALING TECHNOLOGY®, R&D SYSTEMS®, and the like.

An antibody that specifically binds to both the phosphorylated and unphosphorylated ERK and AKT/PTEN signaling pathways polypeptide can be used to measure the level of the total polypeptide in a sample. One skilled in the art recognizes that such antibodies commercial available from, e.g., ABCAM®, CELL SIGNALING TECHNOLOGY®, R&D SYSTEMS®, SANTA CRUZ BIOTECHNOLOGY®, THERMO FISHER SCIENTIFIC®, etc.

Methods for measuring the level of phosphorylated and total protein include, but are not limited to, western blot analysis, enzyme linked immunosorbent assay, immunocytochemistry, flow cytometric analysis, and tandem mass spectrometry. For example, the level of phospho-ERK protein can be detected using an antibody that recognizes Thr202/Tyr204 of ERK1 (Cat. No. #9101; CELL SIGNALING)TECHNOLOGY® in a western blot assay. In some embodiments, the level of phospho-ERK is determined by quantitative western blot which can be performed, for example, using a detection system such as the ODYSSEY® Imager (LI-COR) and following the manufacturer's instructions.

Phosphorylated polypeptides can be measured using liquid chromatography and mass spectrometry. For example, such polypeptide present a protein extract can be separated by nano-flow liquid chromatography using microcapillary columns equipped with integrated electrospray emitter tips attached to a mass spectrometer, such as a hydrid linear ion trap-Orbitrap mass spectrometer.

In some embodiments, the method of step (b) further comprises normalizing the level of phosphorylated and/or total ERK signaling polypeptide to the level of a control polypeptide. Non-limiting examples of a control polypeptide are actin, GAPDH, tubulin or another housekeeping protein. Normalizing the level of phosphorylated polypeptide to a control polypeptide may be needed in order to compare polypeptide levels of a plurality of samples.

The present invention is based, in part, on the discovery of a mathematical model that integrates the activity of two signaling pathways, e.g., RAS/ERK and AKT/PI3K pathways to predict whether a subject has ASD. The mathematical model represented as a biomarker value measures the sum of squares of the subtracted ratios between a test subject and a control of the abundance of phosphorylated protein over total protein for ERK and PTEN. The sum of squares is then divided over the square of the ration of phosphorylated AKT over total AKT. The biomarker value corresponds to $$\{[(\text{p-ERK/ERK})_{patient} - (\text{p-ERK/ERK})_{control}]^2 + [(\text{p-PTEN/PTEN})_{patient} - (\text{p-PTEN/PTEN})_{control}]^2\} / [(\text{p-AKT/AKT})_{patient}]^2.$$

The calculated biomarker value and the control value can be represented on a natural log scale. In some embodiments, if the individual's biomarker value is higher than the control value, it is predicted that the individual has a higher likelihood of having autism spectrum disorder or has an ASD. If the individual's biomarker score is substantially equal to (e.g., substantially the same as) the control value, the individual has a lower risk to have an ASD.

C. Methods of Treating ASD

An autism spectrum disorder symptom includes avoiding eye contact, preferring to play alone, lack of shared interests with other, having flat or inappropriate facial expressions, lack of understanding of personal space boundaries, avoidance/resistance to physical contact, difficulty understanding people's feelings, delayed speech and language skills, abnormal interests and behaviors, need to follow certain routines, display of repetitive motions, hyperactivity, impulsivity, short attention span, aggression, causing self-injury, abnormal mood or emotional reactions, abnormal sensory sensitivity, irritability, and aggression.

Provided herein is a method for treating an individual having or suspected of having ASD by administering an ameliorative treatment to an individual with a calculated biomarker value that is higher than a control value, wherein the calculated biomarker value corresponds to $\{[(p\text{-}ERK/ERK)_{individual} - (p\text{-}ERK/ERK)_{control}]^2 + [(p\text{-}PTEN/PTEN)_{individual} - (p\text{-}PTEN/PTEN)_{control}]^2\}/[(p\text{-}AKT/AKT)_{individual}]^2$. The calculated biomarker value can be obtained by measuring the level of phosphorylated ERK, phosphorylated PTEN, and phosphorylated AKT, and the level of total ERK, total PTEN and total AKT in a sample, e.g., peripheral blood mononuclear cells obtained or isolated from the individual, and performing the mathematical method as described herein. In some embodiments, the method includes administering an ameliorative treatment to the individual who has ASD. The treatment can reduce at least one autism spectrum disorder symptom. The ameliorative treatment may be a non-drug treatment, such as a behavior intervention, a drug-based (pharmaceutical) treatment, or a combination thereof.

Behavior intervention can include, but is not limited to, training methods to decrease or eliminate behaviors that interfering with learning and social functioning, training methods to increase behavior skills that promote communication adaptive, academic and/or vocational skills, positive or negative behavior reinforcement, teaching appropriate behavior skills, discrete trial instruction social scripting/script fading, activity schedules, mand training, video modeling, naturalistic teaching techniques such as in incidental teaching, enhanced milieu teaching, pivotal response training and the like, social skill interventions, imitation training, UCLA/Lovass-based interventions, the Early State Denver Model, the JASPER (joint attention, symbolic play, emotion regulation) program, Children's Friendship Training, and cognitive behavior treatment. Descriptions of other behavior interventions are disclosed in, for example, Weitlauf et al., "Therapies for Children with Autism Spectrum Disorder", Rockville (MD): Agency for Healthcare Research and Quality (US), 2014, Report No. 14-EHC036-EF, Klinger et al., Dialogoues Clin Neurosci, 2013, 15(2):225-233.

In some embodiments, the drug treatment is a method of modulating the level of a phosphorylated ERK signaling polypeptide or reducing ERK activity. The ameliorative treatment method can modulate the level of a phosphorylated PTEN signaling polypeptide or reducing PTEN activity in the individual. Optionally, the ameliorative treatment method can modulate the level of a phosphorylated AKT signaling polypeptide or reducing AKT activity.

In some embodiments, the individual with ASD is administered an ERK modulator, an ERK pathway modulator, a PTEN modulator, a PTEN pathway modulator, an AKT modulator, an AKT pathway modulator, or any combination thereof. An ERK inhibitor, an ERK pathway modulator, a PTEN modulator, a PTEN pathway modulator, an AKT modulator, an AKT pathway modulator, or any combination thereof can be administered to the individual.

The term "inhibitor," "activator," and "modulator" of a protein of interest refers to inhibitory, activating, or modulating molecules, respectively, identified using in vitro and in vivo assays for protein binding or signaling, e.g., ligands, agonists, antagonists, and their homologs and mimetics. The term "modulator" includes inhibitors and activators. Inhibitors are agents that, e.g., partially or totally block carbohydrate binding, decrease, prevent, delay activation, inactivate, desensitize, or down regulate the activity of the protein of interest. In some cases, the inhibitor directly or indirectly binds to the protein, such as a neutralizing antibody. Inhibitors, as used herein, are synonymous with inactivators and antagonists. Activators are agents that, e.g., stimulate, increase, facilitate, enhance activation, sensitize or up regulate the activity of the protein. Modulators include protein binding partners, including modifications of naturally-occurring binding partners and synthetically-designed binding partners, antibodies and antibody fragments, antagonists, agonists, small molecules including carbohydrate-containing molecules, siRNAs, RNA aptamers, and the like.

Methods for decreasing the level of one or more phosphorylated ERK signaling polypeptides include administering a therapeutic agent comprising an ERK inhibitor or any compound that inhibits a signaling pathway involving ERK. Non-limiting examples of an ERK inhibitor include hypericin, 3-(3-amino-2H-pyrazolo[3,4-c]pyridazin-5-yl)-2-phenyl-3H-pyrazolo[1,5-a]pyridin-8-ium (FR 180204), N-methyl-3-phenyl-3-[4-(trifluoromethyl)phenoxy]propan-1-amine fluoxetine, 2-chloro-4-{[2-{ [(2R)-1-hydroxy-3-methylbutan-2-yl]amino}-9-(propan-2-yl)-9H-purin-6-yl]amino}benzoic acid (purvalanol), PD173074, SCI (Pluripotin), GW5074, BAY 43-9006, AG 99, CAY10561, ISIS 5132, Apigenin, SP600125, SU4984, SB203580, PD169316, and/or ERK activation inhibitor peptides, AG1478, 3-cyano-4-(phenoxyanilno)quinolones, and a peptide corresponding to the amino-terminal 13 amino acids of MEK1 and GDC-0994. Detailed description of ERK inhibiting compound that are useful in the present invention can be found in, e.g., WO 2012/019113.

A compound that inhibits the ERK signaling pathway but not directly ERK includes but is not limited to an inhibitor of MEK, ERK1, ERK2, A-RAF, B-RAF, C-RAF, MEK1, MEK2, RSK1, RSK2, RSK3 and RSK4. Non-limiting examples of a MEK inhibitor include 2-(2-amino-3-methoxyphenyl)-4H-chromen-4-one (PD98059), (2Z,3Z)-bis{amino[(2-aminophenyl)sulfanyl]methylidene}butanedinitrile (U0126), 5-[(4-bromo-2-chlorophenyl)amino]-4-fluoro-N-(2-hydroxyethoxy)-1-methyl-1H-benzimidazole-6-carboxamide (AZD6244 (ARRY-142886)), 2-[(2-fluoro-4-iodophenyl)amino]-N-(2-hydroxyethoxy)-1,5-dimethyl-6-oxo-1,6-dihydropyridine-3-carboxamide (or 2-(4-chloro-2-fluoro-anilino)-N-(2-hydroxyethoxy)-1,5-dimethyl-6-oxo-pyridine-3-carboxamide) AZD8330 (ARRY-424704), 2-[(2-chloro-4-iodophenyl)amino]-N-(cyclopropylmethoxy)-3,4-difluorobenzamide (CI-1040), (3R,4R)-4-(3,4-Dimethoxybenzyl)-3-(4-hydroxy-3-methoxybenzyl)dihydrofuran-2

(3H)-one (Arctigenin), (2Z)-3-amino-3-[(4-aminophenyl)sulfanyl]-2-[2-(trifluoromethyl)phenyl]prop-2-enenitrile (SL327), and perillyl alcohol or [(4S)-4-(prop-1-en-2-yl)cyclohex-1-en-1-yl]methanol, U0125(1,4-Diamino-2,3-dicyano-1,4-Ws(phenylthio)butadiene), PD 0325901, AS703026, ARRY-438162, GDC-0973, GSK1120212, R04987655, RDEA119, TAK-733, E6201, CI-1040, PD 318088, PD 0316684, PD 0188563, PD 169842, PD 0335676, PD 0184264, PD184352, ARRY-509, AR-00241389, GC63, G8935, Isothiazole, LL,Z-1640, Hypothemycin, L-783,277, 10-Z-Hymenialdisine, RO-09-2210, 87-250940, XL-518, AR119, AS-701173, AS-701255, 360770-54-3, NAMI-A, 6-(4-Bromo-2-chloro-phenylamino)-7-fluoro-3 (tetrahydro-pyran-2-ylmefhyl)-3H-benzoimidazole-5 carboxylic acid (2-hydroxy-ethoxy)-amide, 1-[6-(4-Bromo-2-chloro-phenylamino)-7-fluoro-3 methyl-3H-benzoimidazol-5-yl]-2-hydroxy-ethanone, 6-(4-Bromo-2-chloro-phenylamino)-7-fluoro-3 methyl-3H-benzoimidazole-5-carboxylic acid (2-hydroxy-1,1-dimethyl-ethoxy)-amide, 6-(4-Bromo-2-chloro-phenylamino)-7-fluoro-3 (tetrahydro-furan-2-ylmethyl)-3H-benzoimidazole-5-carboxylic acid (2-hydroxy-ethoxy)-amide, 6-(4-Bromo-2-fluoro-phenylamino)-7-fluoro-3 methyl-3H-benzoimidazole-5-carboxylic acid (2-hydroxy-ethoxy)-amide and 6-(2,4-Dichloro-phenylamino)-7-fluoro-3-methyl 3H-benzoimidazole-5-carboxylic acid (2-hydroxyethoxy)-amide, 6-(4-Bromo-2-chloro-phenylamino)-7-fluoro-3 methyl-3H-benzoimidazole-5-carboxylic acid (2-hydroxy-ethoxy)-amide, referred to hereinafter as MEK inhibitor 1; 2-[(2-fluoro-4-iodophenyl)amino]-N-(2-hydroxyethoxy)-1,5-dimethyl-6-oxo-1,6-dihydropyridine-3-carboxamide; referred to hereinafter as MEK inhibitor 2, 4-(4-bromo-2-fluorophenylamino)-N-(2-hydroxyethoxy)-1,5-dimethyl-6-oxo-1,6-dihydropyridazine-3 carboxamide 4-(4-Bromo-2-fluorophenylamino)-N-(2-hydroxyethoxy)-1,5-dimethyl-6-oxo-1,6-dihydropyridazine-3-carboxamide, 6-(4-Bromo-2-chloro-phenylamino)-7-fluoro-3-methyl-3H-benzoimidazole-5-carboxylic acid (2-hydroxy-ethoxy)-amide, 2-(2-fluoro-4-iodophenylamino)-N-(2-hydroxyethoxy)-1,5-dimethyl-6-oxo-1,6-dihydropyridine-3-carboxamide, 2-{[3-({4-[(5-{2-[(3 fluorophenyl)amino]-2-oxoethyl}-1H-pyrazol-3-yl)amino]quinazolin-7-yl}oxy)propyl](ethyl) amino} ethyl dihydrogen phosphate, olomoucine, 5-iodotubercidin, GDC-0973, binimetinib, and pharmaceutically acceptable salts thereof.

Examples of a PTEN inhibitor include, but is not limited to; bisperoxovanadium compounds, thioredoxin-1, indolecarboxyhc acid salts, nonenal, deltamethrin, (S)-a-cyano-3-phenoxyb enyl(1R)-cis-3-(2,2 dibrom ovinyl)-2,2-dimethyl cyclopropanecarboxylate; alendronate, sodium, trihydrate, N-(9,10-Dioxo-9,10-dihydrophenanthren-2-yl)-2,2-dimethylpropionamide, 5-benzyl-3furylmethyl (1R,S)-cis,trans-chrysanthemate; suramin, sodium salt; 8,8'-[carbonylbis[imino-3, 1phenylenecarbonylimino (4-methyl-3,1-phenylene)carbonylimino]]bis-, hexasodium salt, 4-methoxyphenacyl bromide, 1,4-dimethylendothall, 1,4-dimethyl-7-oxabicyclo[2.2.1]heptane-2,3-dicarboxylic acid, cantharidic acid; 2,3-dimethyl-7-oxabicyclo[2.2.1]heptane-2,3dicarboxylic acid; sodium stibogluconate, antimony sodium gluconate, 3,4-dephostatin, ethyl-, fenvalerat, α-cyano-3-phenoxybenzyl-α-(4-chlorophenyl)isovalerate, α-naphthyl acid phosphate, monosodium salt, β-glycerophosphate, disodium salt, pentahydrate, endothall, 7-oxabicyclo[2.2.1]heptane-2,3 dicarboxylic acid, cypermethrin, (R,S)-a-cyano-3-phenoxybenzyl-3 (2,2-dichlorovinyl)-2,2-dimethylcyclopropanecarboxylate, (1R)-(R)cyano(3-phenoxyphenyl)methyl 3-(2,2-dichlorovinyl)-2,2-dimethylcyclopropanecarboxylate, SF1670, VO-OHpic and pharmaceutically acceptable salts thereof. Additional PTEN inhibitors are described in, e.g., US Application Publication No. 2007/0203098 and 2011/0002877.

Examples of AKT inhibitors include, but are not limited, to clozapine, nelfinavir, 8-[4-(1-aminocyclobutyl)phenyl]-9-phenyl[1,2,4]triazolo[3,41]-1,6-naphthyridin-3(2H)-one, staurosporine, K-252b, Ro-31-8220, A-443654, GSK-690693, lactoquinomycin, AZD6244, AZD5363, alectinib, and ipatasertib, Inhibitors of other AKT pathway polypeptides include, but are not limited to, wortmannin, LY294002, PWT-458, PX-866, SF-1126, NVP-BEZ235, PI103, GDC-0941, PIK-75, TGX-221, AS-605240, IC87114, perifosine, MK-2206, and GSK-2141795, geldanamycin, 17-AAG, 17-DMAG, radicicol, IPI-504, CNF2024, NVP-AUY922, taselisib, GDC-00847, pictilisib, and pharmaceutically acceptable salts thereof. Additional AKT inhibitors are described in, e.g., US Application Publication No. 2014/0221386, 2014/0256691, and Garcia-Echeverria and Sellers, Oncogene, 2008, 27, 551-5526.

The treatment method can include a therapeutic agent alone or in combination with behavior therapy. In some embodiments, the treatment includes administering one or more pharmaceutical drugs. In other embodiments, the treatment further includes behavior modification or education to reduce at least one symptom of autism.

The above-listed therapeutic agents, or pharmaceutically acceptable salts or derivatives thereof, may be formulated into pharmaceutical dosage forms, together with suitable pharmaceutically acceptable carriers, such as diluents, fillers, salts, buffers, stabilizers, solubilizers, etc. The dosage form may contain other pharmaceutically acceptable excipients for modifying conditions such as pH, osmolarity, taste, viscosity, sterility, lipophilicity, solubility etc.

Suitable dosage forms include solid dosage forms, for example, tablets, capsules, powders, dispersible granules, cachets and suppositories, including sustained release and delayed release formulations.

Powders and tablets will generally comprise from about 5% to about 70% active ingredient. Suitable solid carriers and excipients are generally known in the art and include, e.g., magnesium carbonate, magnesium stearate, talc, sugar, lactose, etc. Tablets, powders, cachets and capsules are all suitable dosage forms for oral administration.

Liquid dosage forms include solutions, suspensions and emulsions. Liquid form preparations may be administered by intravenous, intracerebral, intraperitoneal, parenteral or intramuscular injection or infusion. Sterile injectable formulations may comprise a sterile solution or suspension of the active agent in a non-toxic, pharmaceutically acceptable diluent or solvent. Diluents and solvents can include sterile water, Ringer's solution and isotonic sodium chloride solution, etc. Liquid dosage forms also include solutions or sprays for intranasal administration.

Aerosol preparations for inhalation may include solutions and solids in powder form, which may be combined with a pharmaceutically acceptable carrier, such as an inert compressed gas.

Also encompassed are dosage forms for transdermal administration, including creams, lotions, aerosols and/or emulsions. These dosage forms may be included in transdermal patches of the matrix or reservoir type, which are generally known in the art.

Pharmaceutical preparations may be conveniently prepared in unit dosage form, according to standard procedures of pharmaceutical formulation. The quantity of active compound per unit dose may be varied according to the nature of the active compound and the intended dosage regime. Generally, this will be within the range 0.1 mg to 1000 mg.

In some embodiments, behavior intervention therapy is applied in conjunction with or as an alternative to a pharmaceutical treatment. Behavior therapy can include applied behavior analysis, occupational therapy, physical therapy and speech-language therapy. Applied behavior analysis is a program that to uses a one-on-one teaching approach that encourages positive behaviors and discourages negative behaviors in order to improve a variety of skills. Treatment and Education of Autistic and related communication-handicapped children (TEACCH) is a therapy that uses visual cues to teach skills.

D. Systems and Kits

Provided herein is a system for predicting whether an individual has ASD. Such a system can include a reagent that specifically detects phosphorylated ERK; a reagent that specifically detects total ERK; a reagent that specifically detects phosphorylated PTEN; a reagent that specifically detects total PTEN; a reagent that specifically detects phosphorylated AKT; a reagent that specifically detects total AKT; and a computer readable medium that includes instructions for (a) determining the ratio of (i) phosphorylated ERK to total ERK and (ii) phosphorylated PTEN to total PTEN and calculating the differences of those ratios from corresponding normal healthy ratios thereby generating a measure of difference of phosphorylated ERK and PTEN compared to controls (e.g., determining $\{[(p\text{-}ERK/ERK)_{patient}-(p\text{-}ERK/ERK)_{control}]^2+[(p\text{-}PTEN/PTEN)_{patient}-(P\text{-}PTEN/PTEN)_{control}]^2\}$); (b) comparing said measure to a ratio of phosphorylated AKT to total AKT of the individual, thereby generating a biomarker value (e.g., $\{[(p\text{-}ERK/ERK)_{patient}-(p\text{-}ERK/ERK)_{control}]^2+[(p\text{-}PTEN/PTEN)_{patient}-(p\text{-}PTEN/PTEN)_{control}]^2\}/[(p\text{-}AKT/AKT)_{patient}]^2$); and comparing the biomarker value to a control value.

Provided herein is also a kit for predicting whether an individual has ASD. Such a kit can include a reagent that specifically detects phosphorylated ERK (e.g., an anti-pERK antibody); a reagent that specifically detects total ERK (e.g., an anti-total ERK antibody); a reagent that specifically detects phosphorylated PTEN (e.g., an anti-pPTEN antibody); a reagent that specifically detects total PTEN (e.g., an anti-total PTEN antibody); a reagent that specifically detects phosphorylated AKT (e.g., an anti-pAKT antibody); a reagent that specifically detects total AKT(e.g., an anti-total AKT antibody).

IV. Example

Example 1. Diagnosing Autism Spectrum Disorder in Young Patients

This example illustrates a method for determining whether a human subject has an autism spectrum disorder. The method is based, in part, on determining the level (amount) of phosphorylated proteins of the ERK and AKT signaling pathways relative to the level of the corresponding total proteins in a sample. The sample can be sample comprising peripheral blood mononuclear cells.

Blood samples were obtained from children with ASD and age-matched controls (20 patients and 21 controls). Peripheral blood mononuclear cells (PBMCs) were isolated from the samples over ficoll-hypaque via density centrifugation. Cells were washed 3×, counted and placed in a Trizol solution and stored at −80° C. to stabilize proteins and post-translational modifications. RNA and DNA were removed using RNase and DNase, respectively. The proteins were precipitated and the protein extract (in solution with protease and phosphatase inhibitors) was solubilized with 10 M Urea/50 mM DTT. The extract will be quantified, run on a Western blot (phospho-specific antibody and antibodies to detected total protein) and protein abundance was quantified using the LI-COR imaging platform.

Figure 1B:
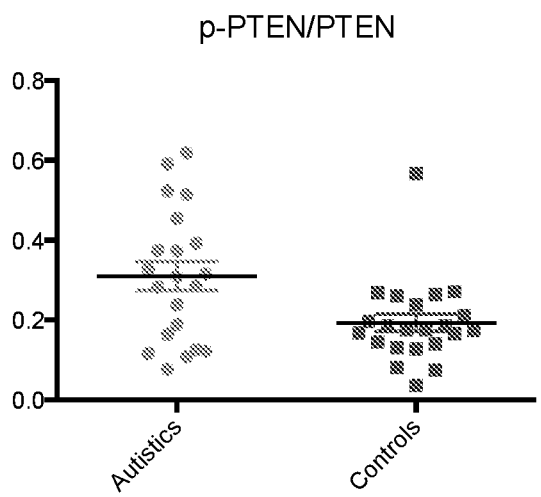
Figure 1C:
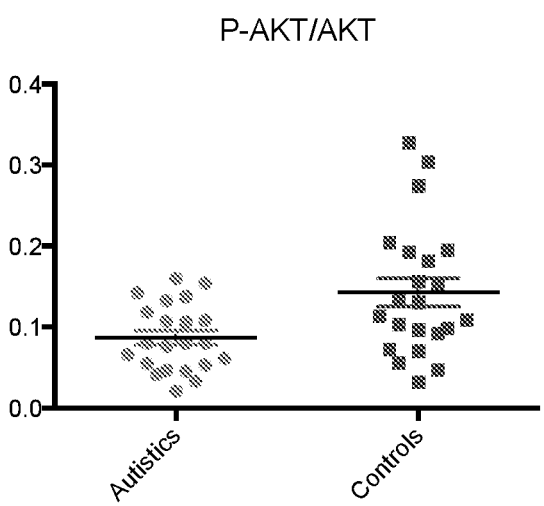

In the patients studied p-ERK levels deviated either above or below the mean levels for the controls. FIGS. 1A-1C show that the mean ratios of p-ERK/ERK, p-PTEN/PTEN and p-AKT/AKT were different for the subjects with ASD versus controls.

By applying the following formula that incorporates the levels of phosphorylated and total ERK, PTEN and AKT:

$$\text{Biomarker value}=\{[(pERK/ERK)_{patient}-(pERK/ERK)_{control}]^2+[(pPTEN/PTEN)_{patient}-(pPTEN/PTEN)_{control}]^2\}/[(pAKT/AKT)_{patient}]^2,$$

Figure 2:
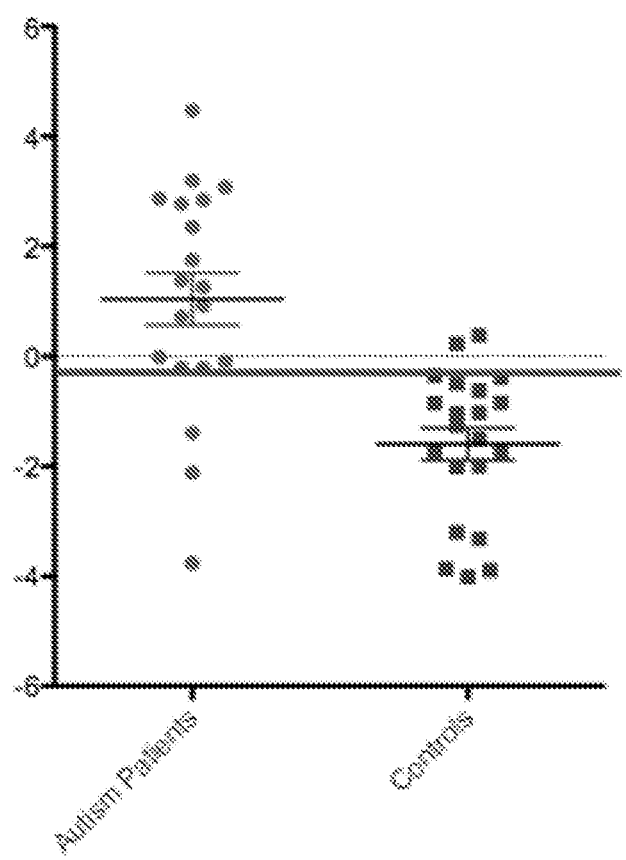
FIG. 2 shows a plot of biomarker measurements (ratios of pERK/total ERK,p-PTEN/total PTEN, and p-AKT/total AKT) in 20 ASD patients and 21 matched controls, displayed on the Y-axis in natural log scale.

ASD patients (n=20) were differentiated from group matched controls (n=21; p<0.0001). A plot of the biomarker values determined for the patients with ASD and healthy controls is shown in FIG. 2 Samples with a biomarker value of >0 were more likely from a patient with ASD and samples with a biomarker value of <0 were more likely to be from a healthy control. Logistic regression modeling using the ratios of fraction phosphorylated PTEN, AKT, AND ERK compared to total protein showed that the assay is highly sensitive for diagnosing patients with ASD.

In summary, the data provided herein shows that a biomarker value derived from the levels of phosphorylated and total ERK, PTEN and AKT, and the formula provided herein can be used to predict whether a child is likely to have or has an ASD.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method of treating an autism spectrum disorder in a human individual, said method comprising the steps of:
   (a) determining that the human individual has an increased likelihood of having the autism spectrum disorder by
      obtaining or having obtained a sample from the human individual;
      performing or having performed an assay to detect the quantity of phosphorylated and total amounts of ERK, PTEN and AKT protein in the sample calculating the ratio of (i) phosphorylated ERK to total ERK and (ii) phosphorylated PTEN to total PTEN;
      calculating the difference of the ratios from corresponding normal healthy control ratios according to a formula $\{[(p\text{-}ERK/ERK)_{patient}-(p\text{-}ERK/ERK)_{control}]^2+[(p\text{-}PTEN/PTEN)_{patient}-(p\text{-}PTEN/PTEN)_{control}]^2\}$, thereby generating a measure of difference of phosphorylated ERK and PTEN compared to control;
      comparing said measure to a ratio of phosphorylated AKT to total AKT of the individual, thereby generating a biomarker value; wherein the biomarker value equals $\{[(p\text{-}ERK/ERK)_{patient}-(p\text{-}ERK/ER-}$ $K)_{control}]^2 + [(\text{p-PTEN/PTEN})_{patient} - (\text{p-PTEN/PTEN})_{control}]^2\} / [(\text{p-AKT/AKT})_{patient}]^2$; and analyzing the biomarker value relative a control value; and (b) identifying a biomarker value that is higher than the control value, and then administering a behavior intervention therapy to the human individual.

2. The method of claim 1, wherein the sample comprises peripheral blood mononuclear cells (PBMCs).

3. The method of claim 1, further comprising testing the individual for behavior or other symptoms indicative of the presence of autism spectrum disorder.

* * * * *